(12) United States Patent
Danzl et al.

(10) Patent No.: US 7,477,943 B2
(45) Date of Patent: Jan. 13, 2009

(54) MEDICAL DEVICE AND METHOD OF MANUFACTURING

(75) Inventors: Ralph B. Danzl, Tempe, AZ (US); Mark R. Boone, Gilbert, AZ (US); Paul F. Gerrish, Phoenix, AZ (US); Michael F. Mattes, Chandler, AZ (US); Tyler Mueller, Phoenix, AZ (US); Jeff Van Wagoner, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 265 days.

(21) Appl. No.: 10/723,016

(22) Filed: Nov. 26, 2003

(65) Prior Publication Data
US 2005/0113895 A1    May 26, 2005

(51) Int. Cl.
*A61N 1/39* (2006.01)
(52) U.S. Cl. .............................................. 607/5; 607/36
(58) Field of Classification Search ................ 607/1–76
See application file for complete search history.

(56) References Cited

U.S. PATENT DOCUMENTS

| | | | |
|---|---|---|---|
| 4,561,906 A | 12/1985 | Calder et al. | |
| 4,642,666 A | 2/1987 | Lidow et al. | |
| 4,723,197 A | 2/1988 | Takiar et al. | |
| 4,823,796 A * | 4/1989 | Benson | 607/7 |
| 5,753,529 A | 5/1998 | Chang et al. | |
| 5,757,081 A | 5/1998 | Chang et al. | |
| 5,767,578 A | 6/1998 | Chang et al. | |
| 5,841,197 A | 11/1998 | Adamic | |
| 5,914,522 A * | 6/1999 | Aiello et al. | 257/500 |
| 5,949,140 A * | 9/1999 | Nishi et al. | 257/728 |
| 6,084,284 A | 7/2000 | Adamic, Jr. | |
| 6,124,179 A | 9/2000 | Adamic, Jr. | |
| 6,221,693 B1 | 4/2001 | Ho | |
| 6,626,931 B2 | 9/2003 | Milla et al. | |
| 6,657,274 B2 * | 12/2003 | Comeau et al. | 257/500 |
| 2003/0213605 A1 * | 11/2003 | Brendel et al. | 174/35 R |

* cited by examiner

*Primary Examiner*—George R Evanisko
*Assistant Examiner*—Michael Kahelin
(74) *Attorney, Agent, or Firm*—Carol F. Barry (57) ABSTRACT

Methods and apparatus are provided for manufacturing a medical device. An implantable medical device includes a semiconductor substrate, an epitaxial layer, and a power transistor. The epitaxial layer overlies the semiconductor substrate. The power transistor is formed in the epitaxial layer and includes a first electrode, a control electrode, and a second electrode. The power transistor has a voltage breakdown greater than 100 volts. The current flow of the power transistor is vertical through the epitaxial layer to the semiconductor substrate. A backside contact couples to the first electrode of the power transistor. A method of manufacturing a medical device includes a power transistor formed in an epitaxial layer overlying a semiconductor substrate. A deep trench is etched through the epitaxial layer exposing the semiconductor substrate. A first electrode contact region couples to an exposed area of the semiconductor substrate in the deep trench.

13 Claims, 9 Drawing Sheets

Figure 1:
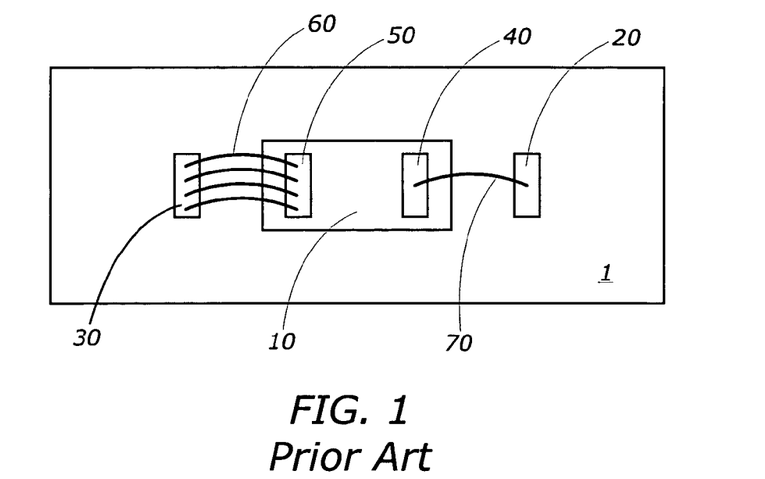
FIG. 1 is a top view of a prior art power transistor coupled to a substrate for use in a medical device.

FIG. 15

MEDICAL DEVICE AND METHOD OF MANUFACTURING

TECHNICAL FIELD OF THE INVENTION

The present invention generally relates to medical equipment, and more particularly relates to medical electrical leads for stimulating biological tissue.

BACKGROUND OF THE INVENTION

A defibrillator is a medical device used to discharge a substantial amount of energy into cardiac tissue. The defibrillator is used to arrest a potentially life-threatening tachyarrhythmia. Defibrillators take many different forms, for example, one type is a unit where all components are external to the patient. The components are portable allowing it to be brought to the patient. Moreover, it can be used on a number of different patients. Defibrillators are also implantable devices placed subcutaneously in the patient as a dedicated system for the patient. An implantable defibrillator has the benefit of detecting a tachyarrhythmia and immediately providing a therapy that arrests the tachyarrhythmia.

In general, a high energy pulse or pulses are applied to the targeted tissue requiring treatment. One common method to generate a high energy pulse is to convert electrical energy from a low voltage/low current source to a high voltage. One approach to achieve this is known as a DC-DC converter. The DC-DC converter utilizes a capacitor and a transformer to generate the high voltage. It should be noted that more than one high voltage signal may be generated using this technique but for illustrative purposes the generation of a single voltage is described. A transformer comprises a primary winding and a secondary winding. The primary winding of the transformer is coupled through a switch to the low voltage power source. Applying a voltage to the primary winding creates a magnetic field that couples the primary winding to the secondary winding. The secondary winding is coupled to a high voltage capacitor for storing energy. Decoupling the primary winding from the voltage source creates a collapsing field that generates a current in the secondary winding that charges the high voltage capacitor. The coupling of energy from the primary winding to the secondary winding is an efficient transfer process. The secondary winding is designed to output a high voltage at low current when the field collapses. The switch coupling the primary winding is repeatedly opened and closed until the high voltage capacitor is charged to a predetermined voltage value.

Defibrillators may use two or more output capacitors to deliver energy in a programmed treatment methodology. The delivery of the energy to the cardiac tissue is coupled through a transistor. The transistor acts a switch. The voltage stored on the capacitor is typically greater than 100 volts. The transistor is enabled and disabled to control when the energy is delivered to the targeted tissue. The transistor used in this type of application is a high voltage transistor such as a power field effect transistor or an insulated gate transistor. The transistor is required to have a high breakdown voltage. For example, transistors with a breakdown between 500 and 1000 volts are used in some implantable defibrillators.

FIG. 1 is a top view of a prior art power transistor 10 coupled to a substrate 1 for use in a medical device. Substrate 1 is a printed circuit board having metal traces for coupling power transistor 10 to other components (not shown) of the medical device. Power transistor 10 has a drain, gate, and a source. Power transistor 10 has a gate contact area 40 and source contact area 50. Substrate 1 respectively has a corresponding gate contact area 20 and a source contact area 60. The drain region of power transistor 10 is the substrate of the device.

Wire bonding is used to couple the gate and source of power transistor 10 to substrate 1. Connections are made to both sides of the die of power transistor 10. As previously stated, the drain is the substrate of power transistor 10. The attachment of power transistor 10 to substrate 1 is an electrical connection of the drain to a drain contact area (not shown) on substrate 1. Electrically conductive epoxy or soldering are two common methods for electrically and physically coupling the substrate (drain) of power transistor 10 to substrate 1. Wire bonding is a mechanical process of attaching one end of a thin wire to a termination point on a side of a die and then attaching the other end of the thin wire to a pad on a substrate. Wire bond 70 couples the gate contact area 40 to the gate contact area 20. Similarly, wire bonds 60 couples the source contact area 50 to source contact area 30. Wire bonds 60 comprise multiple wire bonds to reduce the resistance of the connection. Wire bonds are problematic for medical devices. Wire bonds are fragile elements and the connection process itself can compromise the device which ultimately increases the risk to a patient.

Figure 2:
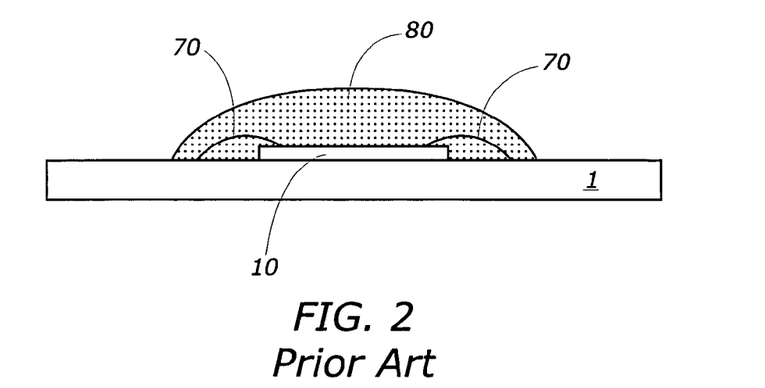
FIG. 2 is a cross-sectional view of prior art substrate 1 and transistor 10 of FIG. 1.

FIG. 2 is a cross-sectional view of prior art substrate 1 and transistor 10 of FIG. 1. In general, transistor 10 is not exposed to the environment after being coupled to substrate 1. An encapsulation material 80 covers and protects power transistor 10. The amount of encapsulation material 80 used is sufficient to cover transistor 10, wire bonds 60, and wire bond 70. A secondary factor is that encapsulation material 80 must cover a vertical height of wire bonds 60 and 70 which is a substantial distance above the upper surface of power transistor 10. As shown, encapsulation material 80 extends beyond the wire bonds 60 and 70. It is highly beneficial to make implantable medical devices as small as possible to reduce invasiveness and to allow the medical device to be located proximal to the targeted tissue. Transistor 10 mounted and packaged on substrate 1 utilizes a significant amount of area as defined by encapsulation material 80. In many medical applications more than one transistor 10 is used further exacerbating the problem.

Accordingly, it is desirable to provide a smaller medical device. In addition, it is desirable to provide a high voltage power transistor capable of standing off voltages exceeding 100 volts that can reduce the footprint when physically and electrically connected to a system substrate. Furthermore, other desirable features and characteristics of the present invention will become apparent from the subsequent detailed description and the appended claims, taken in conjunction with the accompanying drawings and the foregoing technical field and background.

BRIEF SUMMARY OF THE INVENTION

Methods and apparatus are provided for manufacturing a medical device. An implantable medical device includes a semiconductor substrate, an epitaxial layer, and a power transistor. The epitaxial layer overlies the semiconductor substrate. The power transistor is formed in the epitaxial layer and includes a first electrode, a control electrode, and a second electrode. The power transistor has a voltage breakdown greater than 100 volts. The current flow of the power transistor is vertical through the epitaxial layer to the semiconductor substrate. A backside contact couples to the first electrode of the power transistor. A method of manufacturing a medical device includes providing a semiconductor substrate having an epitaxial layer formed thereon. A power transistor having a first electrode, a control electrode, and a second electrode is formed in the epitaxial layer. A deep trench is etched through the epitaxial layer exposing the semiconductor substrate. A first electrode contact region, a control electrode contact region, and a second electrode contact region is formed overlying the epitaxial layer. The first electrode contact region, control electrode contact region, and second electrode contact region respectively couple to the first electrode, control electrode, and second electrode of the power transistor. The first electrode contact region couples to an exposed area of the semiconductor substrate in the deep trench.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 3:
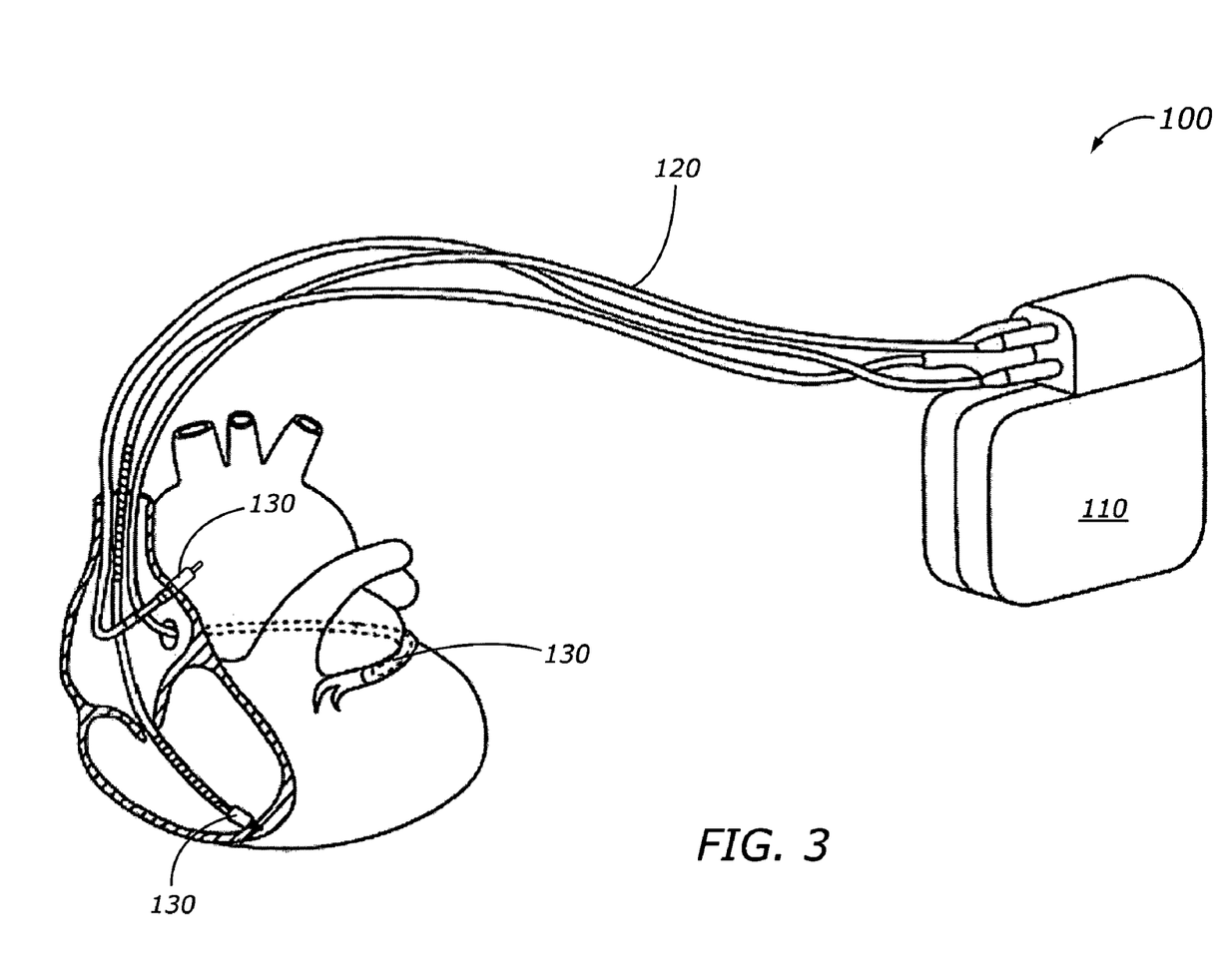
FIG. 3 is an illustration of an implantable medical device 100 in accordance with the present invention.

FIG. 3 is an illustration of an implantable medical device 100 in accordance with the present invention. Implantable medical device 100 provides a high voltage pulse to targeted tissue of a patient. In an embodiment of implantable medical device 100, the targeted tissue is cardiac tissue. Implantable medical device 100 comprises a central control module 110, leads 120, and electrodes 130. Central control module 110, leads 120, and electrodes 130 are subcutaneously implanted in the patient. Central control module 110 typically includes a power source and electronic circuitry for controlling the therapy. Housed within central control module 110 is at least one power transistor (not shown) having a breakdown voltage exceeding 100 volts. The power transistor or power transistors takes up significant space within central control module 110 but are necessary for applications requiring high voltage. An example of a medical device that requires high voltage transistors is a defibrillator.

Leads 120 are coupled to circuitry in central control module 110 to deliver electrical stimulation to the targeted tissue. The body of leads 120 is made of an insulating material to prevent high voltage from a conductor within leads 120 from shorting to untargeted tissue of the patient. At a distal end of leads 120 are electrodes for contacting the targeted tissue. The electrodes make electrical contact with the targeted tissue. As shown, leads 120 couple to different regions of the heart. In operation, implantable medical device 100 is capable of providing high-energy pulses to stimulate cardiac tissue to an appropriate response.

Figure 4:
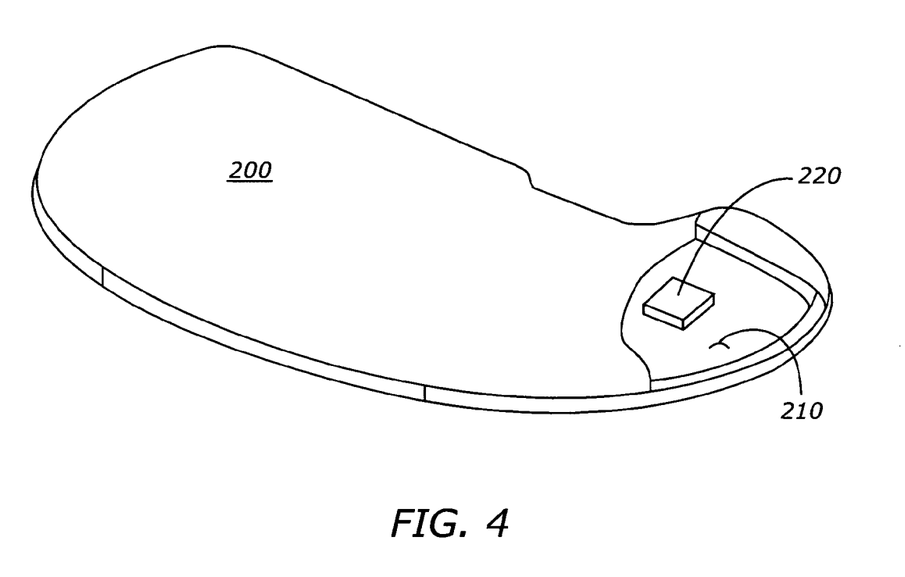
FIG. 4 is a cutaway view of a housing of a portion of an implantable medical device in accordance with the present invention.

FIG. 4 is a cutaway view of a housing 200 of a portion of an implantable medical device in accordance with the present invention. Housing 200 is a sealed enclosure that isolates components of the medical device from the external environment. Within housing 200 are a substrate 210 and at least one high voltage power transistor 220. Substrate 210 is a support surface for mounting high voltage power transistor 220 and may include interconnect for coupling high voltage power transistor 220 to other circuitry (not shown). High voltage power transistor 220 operates at a voltage greater than 100 volts.

High voltage power transistor 220 is a semiconductor die. In general, high voltage power transistor 220 is a three terminal device, for example, a power field effect transistor having a drain, gate, and source. High voltage power transistor 220 is not limited to being a power field effect transistor but can be any high voltage power transistor capable of holding off greater than 100 volts without breaking down. Using a flip chip mounting approach minimizes the space required to mount high voltage power transistor 220. For example, high voltage power transistor 220 as a power field effect transistor would require that the drain, gate, and source contacts be exposed on the same surface of the power transistor die to mount as a flip chip. Solder bumps would be formed on the drain, gate, and source contacts on the same surface of the die. The solder bumps on high voltage power transistor 220 would then be aligned and coupled to contacts on substrate 210. The solder bumps would be reflowed to physically and electrically couple high voltage power transistor 220 to contacts on substrate 210.

Figure 5:
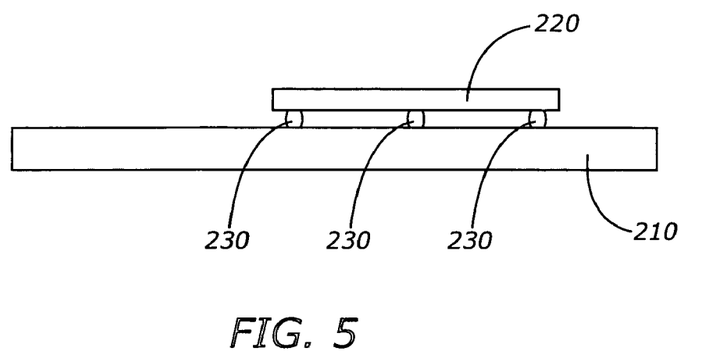
FIG. 5 is a cross-sectional view of high voltage power transistor 220 of FIG. 4 in accordance with the present invention.

FIG. 5 is a cross-sectional view of high voltage power transistor 220 of FIG. 4 in accordance with the present invention. Solder bumps 230 are shown coupling the gate, drain, and source of high voltage power transistor 220 to substrate 200. Solder bumps 230 are aligned to contact areas on substrate 210 then reflowed to physically and electrically couple high voltage power transistor 220 to substrate 210. In one embodiment, high voltage power transistor 220 is flip chipped to substrate 210 with an underfill material (not shown) placed between substrate 210 and the die of high voltage power transistor 220. The underfill material is used to prevent contaminating materials from contacting the surface of high voltage power transistor 220. The underfill material does not extend substantially beyond the edge of the die, thus high voltage power transistor 220 provides a minimum contact area and profile when mounted to substrate 210 thereby reducing the size of a medical device.

Figure 6:
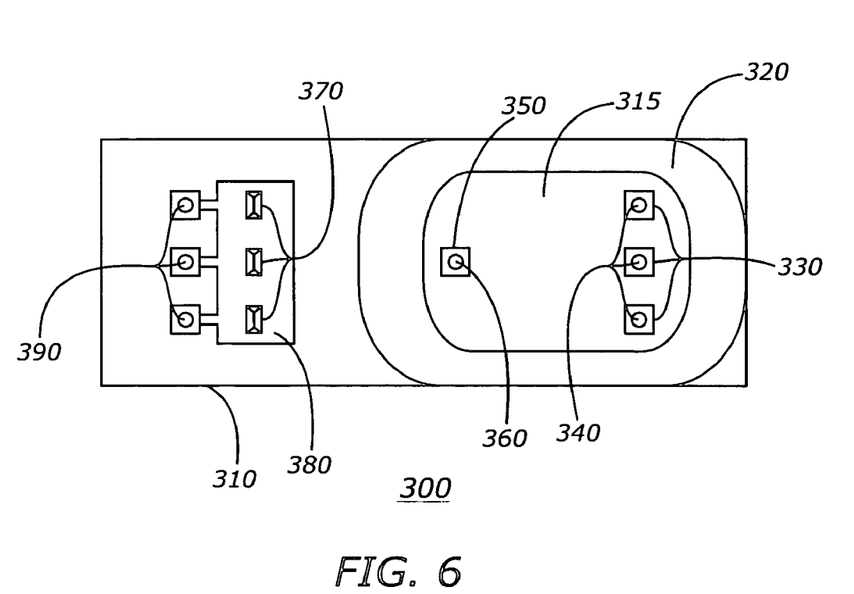
FIG. 6 is a top view of a high voltage power transistor for an implantable medical device in accordance with the present invention.

FIG. 6 is a top view of a high voltage power transistor 300 for an implantable medical device in accordance with the present invention. High voltage power transistor 300 is capable of withstanding greater than 100 volts before breaking down. High voltage power transistor 300 is formed in a semiconductor substrate 310. In an embodiment of high voltage power transistor 300, the device is formed in cells. Each cell is a transistor. The cells are coupled in parallel to form high voltage power transistor 300. The cells of high voltage power transistor 300 are formed in an active area 315 within semiconductor substrate 310. A high voltage termination region 310 surrounds active area 310. High voltage termination region 320 is an isolation region to ensure the high voltage breakdown of the device. For example, in a medical device such as a defibrillator, power transistors having a voltage breakdown of 500 to 1000 volts are often used.

In an embodiment of high voltage power transistor 300, semiconductor substrate 310 is a first electrode of the device. In general, high voltage power transistor 300 is a device structured for substantially vertical current flow from the upper surface of the die through semiconductor substrate 310. Contact regions 330 couple to a second electrode of high voltage power transistor 300. Contact regions 330 comprise more than one area to lower the resistance of the connection. Solder bumps 340 are formed on contact regions 330. In an embodiment, of high voltage power transistor 300, contact regions 330 are located in active area 315. In general, the second electrode couples to the active part of high voltage power transistor 300 that resides on the upper surface of the die.

A contact region 350 couples to the control electrode of high voltage power transistor 300. A solder bump 360 is formed on contact region 350. A voltage applied to the control electrode of high voltage power transistor 300 enables the device to conduct a current between the first and second electrodes. In an embodiment of high voltage power transistor 300, contact region 350 is placed in active area 315.

Trenches 370 are formed in semiconductor substrate 310 to create a backside contact. As mentioned previously, the current flow of high voltage power transistor 300 is vertical through semiconductor substrate 310. Trenches 370 are etched to a depth in semiconductor substrate 310 to contact a low resistance region in semiconductor substrate 310. The low resistance region is not located near the surface of semiconductor substrate 310 to increase voltage breakdown of the device. Contact region 380 is a conductive layer on the surface of semiconductor substrate 310 and within trenches 370. Contact region 380 couples to the low resistance region exposed by trenches 370. In an embodiment of high voltage power transistor 300, trenches 370 and contact region 380 is formed outside active area 310 and high voltage termination region 320. Solder bumps 390 are formed on contact region 380. Thus, high voltage power transistor 300 has the first, control, and second electrodes exposed for flip chip mounting.

Figure 7:
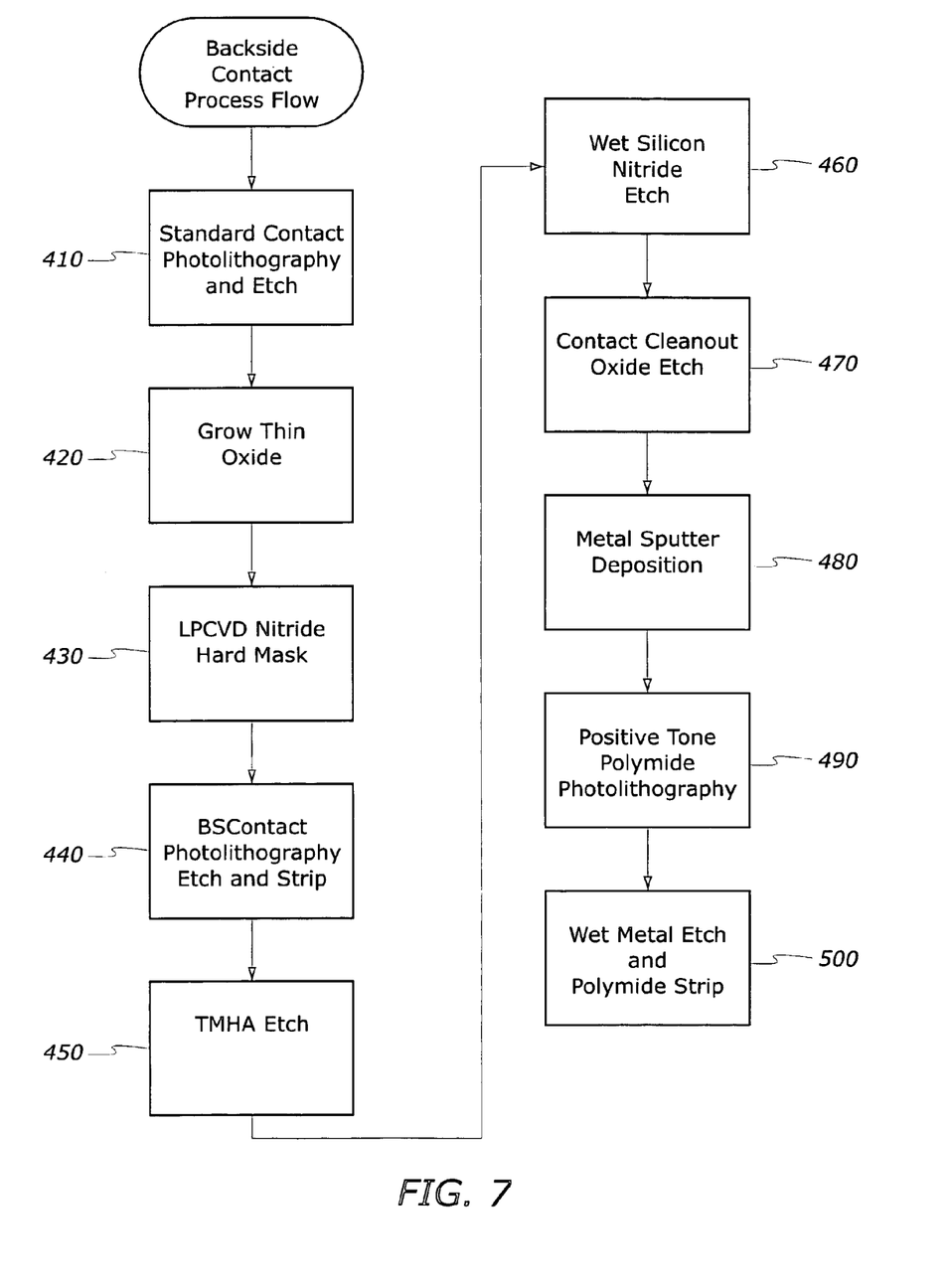
FIG. 7 is a flow diagram to form a backside (BS) contact in a high voltage power transistor for an implantable medical device in accordance with the present invention.

FIG. 7 is a flow diagram to form a backside (BS) contact in a high voltage power transistor for an implantable medical device in accordance with the present invention. The description of the flow diagram will be described in conjunction with FIGS. 8-13 which are cross-sectional views illustrating the formation of the BS contact. It should be appreciated that the implants to form a power transistor are not shown in FIGS. 8-13 to simplify the drawings and the process as described is readily adaptable to different types of high voltage power transistors such as a power field effect transistor or an insulated gate transistor.

Figure 8:
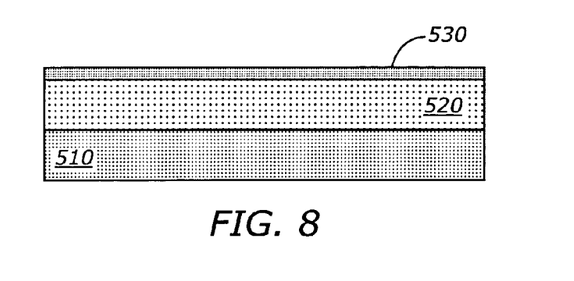
FIG. 8 is an illustration of a semiconductor substrate in accordance with the present invention.

FIG. 8 is an illustration of a semiconductor substrate 510 in accordance with the present invention. In an embodiment of the wafer process, an epitaxial layer 520 is formed on semiconductor substrate 510. Epitaxial layer 520 is of the same type as semiconductor substrate 510 but has a higher resistivity. A high voltage power transistor structure is formed in epitaxial layer 520. The breakdown voltage of the power transistor corresponds to the resistivity and thickness of epitaxial layer 520. Thus, epitaxial layer 520 is chosen in part to ensure the power transistor formed therein has a breakdown that exceeds 100 volts. Semiconductor substrate 510 has a low resistivity to minimize the drain to source resistance ($r_{dson}$) of the power transistor. A layer of phosphosilicate glass (PSG) 530 is formed on the surface of semiconductor substrate 510 that contains field effect transistors. This glass layer acts to getter positively charged ionic contaminants from the upper conductive layers and seal the underlying field effect transistors from these stray charges. It should be noted that the thickness of epitaxial layer 520 and semiconductor substrate 510 are not drawn in proportion to one another. Semiconductor substrate 510 typically has a much greater thickness than epitaxial layer 520.

Figure 9:
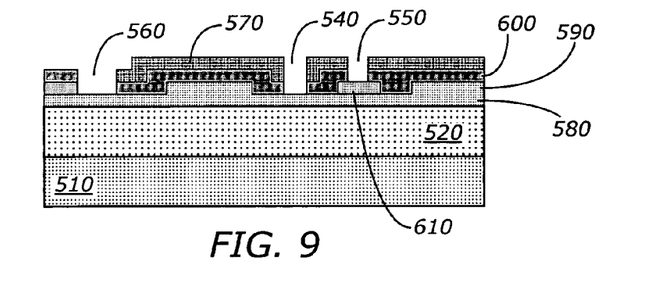
FIG. 9 is an illustration of semiconductor substrate 510 of FIG. 8 patterned and etched to expose contact regions for the first electrode, control electrode, and second electrode of the high voltage power transistor in accordance with the present invention.

FIG. 9 is an illustration of semiconductor substrate 510 patterned and etched to expose contact regions for the first electrode, control electrode, and second electrode of the high voltage power transistor in accordance with the present invention. Step 410 of FIG. 7 is performed in FIG. 9. The high voltage power transistor is a three terminal device having a first electrode, a control electrode, and a second electrode. The control electrode and the second electrode are shallow contacts. The high voltage power transistor has an approximately vertical current path from the second electrode through epitaxial layer 520 to substrate 510 that couples to the first electrode. In general, the major elements of the power transistor, independent of type, are formed before the BS contact. The layers shown are for illustrative purposes to demonstrate processing of the BS contact.

A thin oxide layer 580, a field oxide layer 590, a PSG layer 600, and a polysilicon layer 610 are formed overlying epitaxial layer 520 prior to depositing photoresist layer 570. Thin oxide layer 580, field oxide layer 590, and PSG layer 600 are silicon dioxide layers used to decouple conductive regions from one another. Each of the aforementioned layers is formed and patterned during the wafer process to yield the structure as shown. In particular, thin oxide layer 580, as it name implies is a thin layer of silicon dioxide that forms a gate dielectric layer. Polysilicon layer 610 overlies thin oxide layer 580 to form the control electrode of the high voltage power transistor.

A photoresist layer 570 is formed overlying thin oxide layer 580, field oxide layer 590, PSG layer 600, and polysilicon layer 610. The photoresist layer 570 is patterned such that photoresist is removed in areas corresponding to contact regions of the first electrode, control electrode, and the second electrode. An etch step is then applied to etch in areas where the photoresist was removed. The etchant removes silicon dioxide. An opening 550 exposes the polysilicon layer 610 corresponding to the control electrode of the power transistor.

An opening 540 is formed that exposes a first region of epitaxial layer 520. The first region exposed by opening 540 corresponds to a contact region of the second electrode of the power transistor. Openings 540 and 550 relate to shallow contacts of the power transistor. Similarly, an opening 560 is formed that exposes a second region of epitaxial layer 520. The second region exposed by opening 560 corresponds to a contact region of the first electrode of the power transistor. In general, openings 540, 550, and 560 are formed simultaneously during the etch step.

Figure 10:
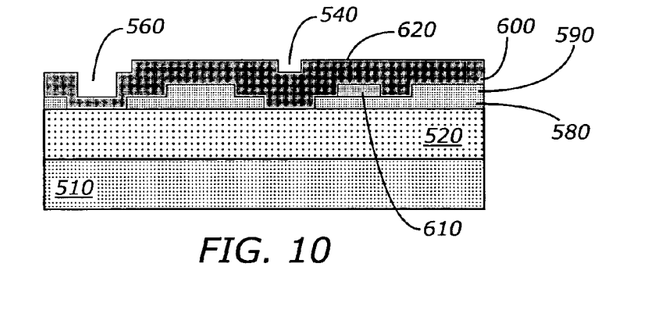
FIG. 10 is an illustration of semiconductor substrate 510 of FIG. 9 including the formation of a nitride/oxide layer in accordance with the present invention.

FIG. 10 is an illustration of semiconductor substrate 510 including the formation of a sacrificial nitride/oxide layer 620 in accordance with the present invention. Steps 420 and 430 of FIG. 7 are performed in FIG. 10. Photoresist layer 570 is removed after etching. A thin oxide layer is formed overlying thin oxide layer 580, field oxide layer 590, PSG layer 600, polysilicon layer 610, and epitaxial layer 520. The oxide layer covers exposed surfaces in openings 540, 550, and 560. The oxide layer acts as a buffer to the hard mask formed next.

A layer of silicon nitride is then formed overlying the oxide layer. Although the silicon nitride and oxide layer are formed in separate steps nitride/oxide layer 620 denotes the combination. In an embodiment of the process, the thickness of the silicon nitride layer and the oxide layer is respectively 1200 angstroms and 75 angstroms. The silicon nitride layer is a hard mask to protect underlying circuitry for a subsequent etch step for the backside contact. The oxide layer acts as a film stress buffer layer between the silicon nitride layer and the underlying silicon.

Figure 11:
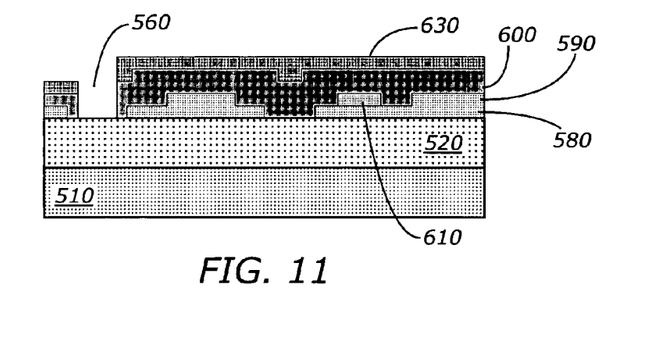
FIG. 11 is an illustration of semiconductor substrate 510 of FIG. 10 where nitride/oxide layer 620 is patterned.

FIG. 11 is an illustration of semiconductor substrate 510 where nitride/oxide layer 620 is patterned. Step 440 is performed in FIG. 11. A photoresist layer 630 is formed and patterned overlying nitride/oxide layer 620. Photoresist layer 630 is patterned such that no photoresist is in opening 560 thereby leaving the silicon nitride layer exposed therein. The silicon nitride layer in opening 560 is etched away exposing the underlying thin oxide layer. The thin oxide layer in opening 560 is then etched away exposing epitaxial layer 520. Photoresist layer 630 is then removed.

Figure 12:
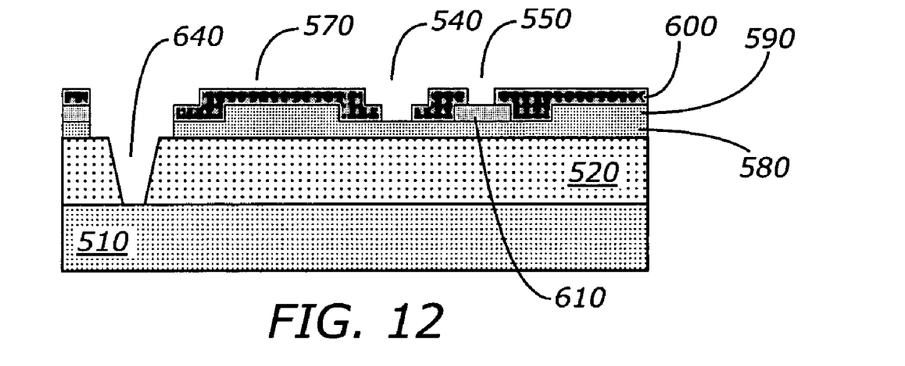
FIG. 12 is an illustration of semiconductor substrate 510 of FIG. 11 showing a deep trench formed through epitaxial layer 520 that extends to semiconductor substrate 510.

FIG. 12 is an illustration of semiconductor substrate 510 showing a deep trench 640 formed through epitaxial layer 520 that extends to semiconductor substrate 510. Steps 450, 460, and 470 of FIG. 7 are performed in FIG. 12. An etch step is performed to etch deep trench 640 in an area corresponding to opening 560. In an embodiment of the etch step, a TMAH etch is used to form deep trench 630 by etching in a <100> crystal orientation. The dimensions of the trench width are controlled by the thickness of epitaxial layer 520. For example, there is a geometric relationship for a right triangle whereby the angle <111> (side) to the <100> (top of the silicon) is 54.7 degrees. Therefore, if the depth of the trench is, for example 100microns represented by the base, and the opposite angle is 35.3 degrees as determined by the sum of the angles, then the opposite side will be (tan 35.3)×100 microns, or 71 microns, and the total opening will be 142 microns. As mentioned previously, although a single trench is shown being etched, the power transistor may have more than one deep trench for the backside contact.

The TMAH etch is a lengthy etch due to distance to semiconductor substrate 510. For example, the etch rate is approximately 0.7 microns/minute at 70 degrees Centigrade. For example, 2 to 3 hours of etch time may be required for thick epitaxial layers (100 microns or more) used for power transistors having 500-1000 volt breakdowns. The etch produces a tapered trench as shown. Upon reaching semiconductor substrate 510, the etch is continued to expose a sufficient area to produce a low resistance contact for the first electrode of the power transistor. A wet silicon nitride etch is performed to remove the silicon nitride layer after deep trench 640 is formed. A contact clean out is then performed to remove any oxide in openings 540, 550, and deep trench 640.

Figure 13:
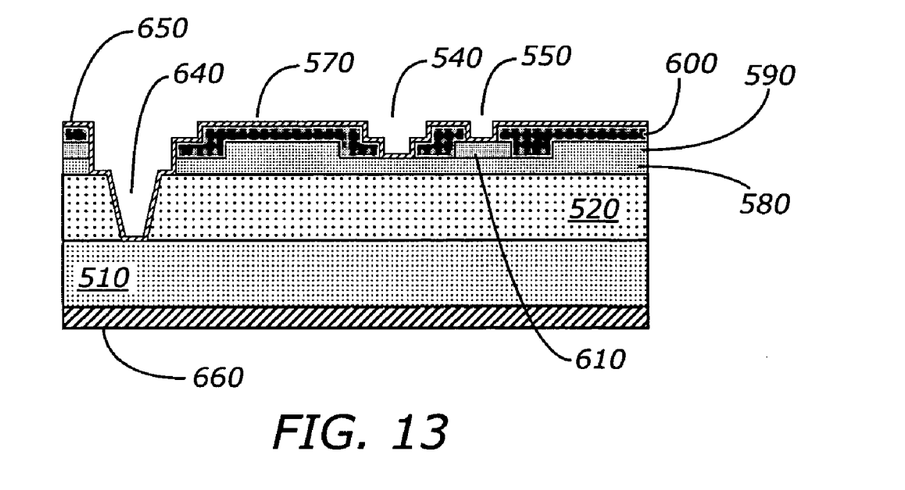
FIG. 13 is an illustration of semiconductor substrate 510 of FIG. 12 showing deposition of a metal layer to contact the first electrode, control electrode, and the second electrode of the power transistor.

FIG. 13 is an illustration of semiconductor substrate 510 showing deposition of a metal layer 650 to contact the first electrode, control electrode, and the second electrode of the power transistor. The metal contact regions of the first, control, and second electrodes are formed on a same side of semiconductor substrate 510 to allow solder bumping and flip chip mounting into an implantable medical device. Steps 480, 490, and 500 of FIG. 7 are performed in FIG. 13.

Metal layer 650 is deposited overlying thin oxide layer 580, field oxide layer 590, PSG layer 600, polysilicon layer 610, epitaxial layer 520, and semiconductor substrate 510. Metal layer 650 is subsequently patterned to form interconnect of the high voltage power transistor including the contact regions of the first, control, and second electrodes of the power transistor. The metal contact regions further include areas for receiving solder bumps. Metal layer 650 also resides on the side walls and bottom area of deep trench 640. Thus, the metal contact region of the first electrode extends into deep trench 640 directly contacting semiconductor substrate 510. Metal layer 650 couples to polysilicon layer 610 through opening 550 corresponding to the control electrode and epitaxial layer 520 through opening 540 corresponding to the second electrode of the high voltage power transistor.

Deep trench 640 is problematic for a patterning process because of its size and depth. In an embodiment of the wafer process, a direct pattern technique that involves a thick layer (12 microns) of positive tone polyimide is used to mask off areas where the metal is to remain. The positive tone polyimide is both conformal and protective to prevent removal of the metal in deep trench 640. The positive tone polyimide is removed (patterned) in areas to expose metal layer 650. The exposed metal is then etched away. The positive tone polyimide is stripped away leaving metal contact regions coupled to the first, control, and second electrode of the power transistor. A metal layer 660 on a backside of semiconductor substrate 510 can be added to further lower the resistance path to the first electrode. An alternate methodology for forming and patterning the metal layer 650 is to use a metal lift off process.

Figure 14:
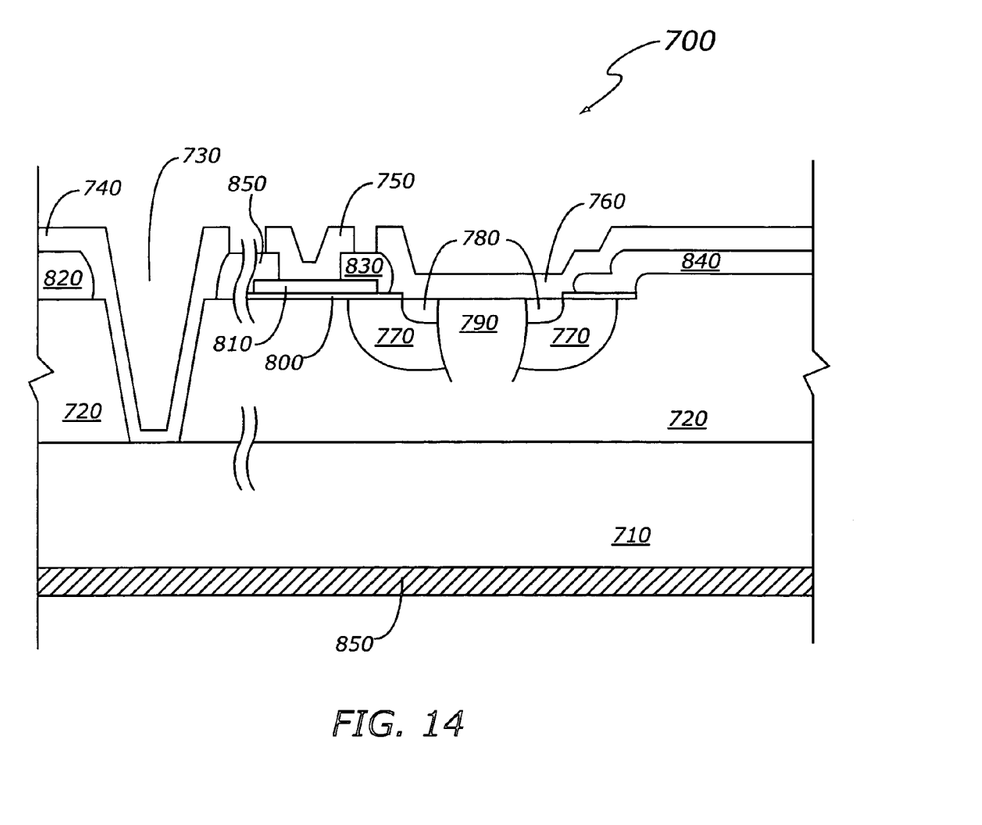
FIG. 14 is an illustration of a power transistor having a backside contact in accordance with the present invention.

FIG. 14 is an illustration of a power transistor 700 having a backside contact in accordance with the present invention. For simplicity, a single transistor cell is shown. Typically, power transistor 700 comprises many transistor cells coupled in parallel. Power transistor 700 includes a drain contact region 740, a gate contact region 750, and a source contact region 760. Drain contact region 740, gate contact region 750, and source contact region 760 comprise a metal or metal alloy layer that includes area for solder bumping such that all interconnect of power transistor 700 are on the same side allowing a flip chip connection to another substrate.

An epitaxial layer 720 is formed on semiconductor substrate 710. In an embodiment of power transistor 700, both epitaxial layer 720 and semiconductor substrate 710 are n-type. A thickness and resistivity of epitaxial layer 720 is a determining factor in the breakdown voltage of power transistor 700. Semiconductor substrate 710 has a lower resistivity than epitaxial layer 720 and is a low resistance current path. A deep trench 730 is etched through epitaxial layer 720 exposing semiconductor substrate 710. Drain contact region 740 covers the sidewalls and bottom of deep trench 730 electrically coupling to epitaxial layer 720 and semiconductor substrate 710. Isolation regions 820, 830, 840, 850 are a thick dielectric layer typically comprising silicon dioxide. A portion of drain contact region 740 is formed over isolation region 820. Drain contact region 740 is separated from gate contact region 750 by isolation region 850.

Power transistor 700 conducts current in a vertical path through epitaxial layer 720. The current then travels laterally through semiconductor substrate 710 to drain contact region 740. In an embodiment of power transistor 700, more than one deep trench 730 is formed to ensure a low contact resistance with semiconductor substrate 710. It should be noted that deep trench 730 is spaced a sufficient distance from the transistor cells that comprise power transistor 700 such that it is not the limiting factor in voltage breakdown. Drain contact region 740 includes an area or areas for receiving solder bumps.

Source contact region 760 couples to an upper surface of epitaxial layer 720. Source contact region 760 includes area or areas for receiving solder bumps. A p-tub 770 is formed in epitaxial layer 720 underlying source contact region 760. An n-region 780 is formed in p-tub 770 underlying source contact region 760. A p-region 790 is formed in n-region 780 and p-tub 770 underlying source contact region 760. N-region 780 and p-region 790 are heavily doped for low resistance and are electrically coupled together by source contact region 760. Voltage breakdown of power transistor 700 occurs between epitaxial layer 720 and p-tub 770. A portion of source contact region 760 overlies isolation region 840. Gate contact region 750 is separated from source contact region 760 by isolation region 830.

A gate oxide 800 is formed on epitaxial layer 720. Gate oxide 800 overlies a portion of p-tub 770. A polysilicon gate 810 overlies gate oxide 800. Gate contact region 750 electrically couples to polysilicon gate 810. Gate contact region includes area for receiving a solder bump. A voltage applied to gate contact region 750 forms an n-type inversion channel in p-tub 770 that couples on one side to n-region 780 and epitaxial layer 720 on the other side. An n-type conductive path is formed comprising semiconductor substrate 710, epitaxial layer 720, the n-type inversion channel in p-tub 770, and n-region 780. A differential voltage applied across drain contact region 740 and source contact region 760 produces current flow through power transistor 700. The magnitude of the current flow is a function of the applied differential voltage from drain contact region 740 to source contact region 760 and the voltage applied to gate contact region 750 to create the n-type inversion channel. A metal layer 850 is formed on semiconductor substrate 710 to further the on resistance of power transistor 700. It should be noted that a p-channel power transistor could similarly be formed as would be understood by one skilled in the art.

Figure 15:
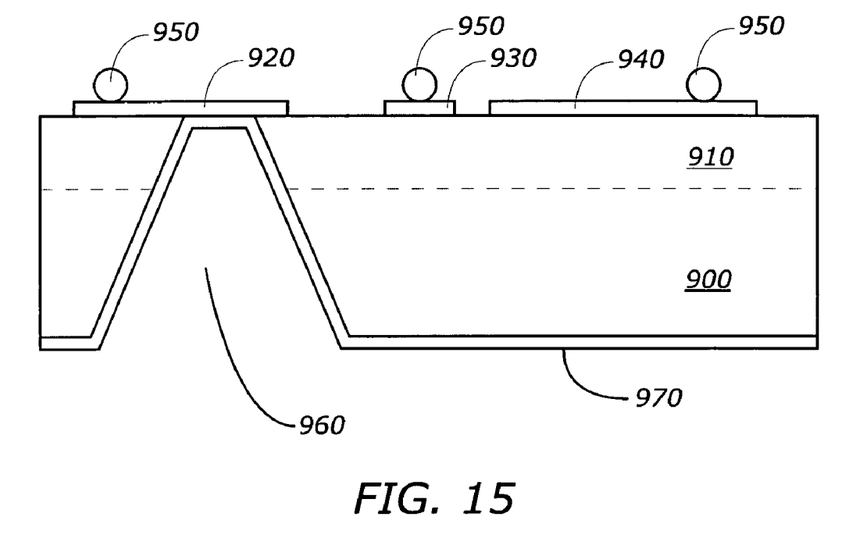
FIG. 15 is an alternate backside contact in accordance with the present invention.

FIG. 15 is an alternate backside contact in accordance with the present invention. A high voltage power transistor (not shown) is formed in an epitaxial layer 910 on a semiconductor substrate 900. The high voltage power transistor has a first electrode, a control electrode, and a second electrode respectively coupled to a first electrode contact region 920, a control electrode contact region 930, and a second electrode contact region 940. First electrode contact region 920, control electrode contact region 930, and second electrode contact region 940 are metal or metal alloy regions overlying epitaxial layer 910 that include area for forming solder bumps 950. Solder bumps 950 are interconnect for the high voltage power transistor to couple the first electrode, control electrode, and second electrode to a substrate (not shown).

Current though high voltage power transistor flows in a vertical path through epitaxial layer 910 and semiconductor substrate 900. Epitaxial layer 910 has a higher resisitivity than semiconductor substrate 900 to increase a breakdown voltage of the high voltage power transistor. In general, the formation of the high voltage power transistor and first electrode contact region 920, control electrode contact region 930, and second electrode contact region 940 occurs prior to the backside contact is created. A tool to identify and align areas on a surface of epitaxial layer 910 is used to target areas on an exposed surface of semiconductor substrate 900. In particular, the exposed surface of semiconductor substrate 900 is masked and patterned for etching. The areas exposed for etching on semiconductor substrate 900 are aligned to first electrode contact region 920. An etch step is initiated that etches through semiconductor substrate 900 and epitaxial layer 910. A deep trench 960 is formed that stops when a sufficient area of first electrode contact region 920 is exposed for reliable electrical contact. It should be noted that a mask is formed overlying epitaxial layer 910 to protect structures formed in and overlying epitaxial layer 910 subsequent to forming the backside contact. A conductive layer 970, for example a metal or metal alloy layer is formed on semiconductor substrate 900 and in deep trench 960. Conductive layer 970 electrically couples epitaxial layer 910 and semiconductor substrate 900 to first electrode contact region 920. Conductive layer 970 is a low resistance conductive path for current in semiconductor substrate 900. The backside contact allows all terminals of the high voltage power transistor to be formed on the same side of the die. The high voltage power transistor is coupled in a flip chip methodology using solder bumps to a substrate of a medical device thereby greatly reducing a footprint of the medical device which is highly beneficial for an implantable device.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An implantable medical device comprising:
  a semiconductor substrate having a top surface;
  an epitaxial layer overlying the semiconductor substrate top surface, the epitaxial layer having a top surface;
  a high voltage termination region formed in the epitaxial layer;
  a power transistor formed in the epitaxial layer having a first electrode, a control electrode, and a second electrode wherein a breakdown voltage of the power transistor is greater than 100 volts and wherein current flow of the transistor is vertical through the epitaxial layer to the semiconductor substrate; and
  a backside contact coupling to the first electrode of the power transistor comprising at least one deep trench etched through the epitaxial layer, the deep trench extending from the epitaxial layer top surface to the semiconductor substrate and exposing the semiconductor substrate top surface wherein the at least one deep trench is etched in an area outside the high voltage termination region.

2. The implantable medical device as recited in claim 1 further including:
  an active area region in the epitaxial layer; and a plurality of transistor cells formed in the active area region wherein the power transistor comprises the plurality of transistor cells electrically coupled in parallel.

3. The implantable medical device as recited in claim 2 wherein the high voltage termination region surrounds the active area region.

4. The implantable medical device as recited in claim 3 wherein the semiconductor substrate has a lower resistivity than the epitaxial layer.

5. The implantable medical device as recited in claim 4 wherein a second electrode contact region couples to a surface of the epitaxial layer in the active area region corresponding to the second electrode.

6. The implantable medical device as recited in claim 5 wherein a control electrode contact region overlies the epitaxial layer in the active area region and couples to the control electrode.

7. The implantable medical device as recited in claim 6 further including solder bumps formed on the first electrode contact region, the control electrode contact region, and the second electrode contact region on the epitaxial layer top surface for flip chip mounting.

8. The implantable medical device as recited in claim 7 further including:
    a housing; and
    a substrate in the housing wherein the solder bumps of the first electrode contact region, the control electrode contact region, and the second electrode contact region are coupled to interconnect on the substrate and wherein the interconnect couples to other circuitry of the implantable medical device.

9. The implantable medical device as recited in claim 8 wherein the implantable medical device is a defibrillator.

10. The implantable medical device as recited in claim 4 wherein the backside contact comprises:
    a conductive layer overlying side walls and a bottom of the deep trench to couple the exposed semiconductor substrate to the first electrode contact region.

11. The implantable medical device of claim 10 wherein the bottom of the deep trench exposes the semiconductor substrate.

12. The implantable medical device of claim 1 wherein the backside contact further comprises multiple deep trenches to provide a low contact resistance with the exposed semiconductor substrate.

13. An implantable medical device comprising:
    a semiconductor substrate having a top surface;
    an epitaxial layer overlying the semiconductor substrate top surface, the epitaxial layer having a top surface and a higher resistance than the semiconductor substrate;
    a high voltage termination region formed in the epitaxial layer;
    a power transistor formed in the epitaxial layer having a first electrode, a control electrode, and a second electrode wherein a breakdown voltage of the power transistor at the high voltage termination region is greater than 100 volts and wherein current flow of the transistor is vertical through the epitaxial layer to the semiconductor substrate; and
    a backside contact comprising
        a first contact region for coupling to the first electrode,
        a second contact region for coupling to the control electrode,
        a third contract region for coupling to the second electrode, and
        at least one deep trench etched outside the high voltage termination region through the epitaxial layer, the deep trench having sidewalls extending from the epitaxial layer top surface to a bottom of the deep trench, the bottom of the deep trench exposing the semiconductor substrate, and
        each of the first, second and third contact regions comprising a metal layer extending over a surface of the power transistor corresponding to the epitaxial layer top surface, the metal layer further extending along the sidewalls and bottom of the deep trench to thereby couple the exposed semiconductor substrate to the first contact region;
    the first, second and third contact regions each comprising solder bumps for flip chip mounting within the implantable medical device.

* * * * *